(12) United States Patent
Shingu et al.

(10) Patent No.: US 6,663,612 B2
(45) Date of Patent: Dec. 16, 2003

(54) DISPOSABLE DIAPER

(75) Inventors: Yoshikazu Shingu, Kagawa-ken (JP); Hirotomo Mukai, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 10 days.

(21) Appl. No.: 09/880,657

(22) Filed: Jun. 13, 2001

(65) Prior Publication Data

US 2001/0053903 A1 Dec. 20, 2001

(30) Foreign Application Priority Data

Jun. 19, 2000 (JP) .................................. 2000-183829

(51) Int. Cl.[7] .............................................. A61F 13/15
(52) U.S. Cl. ...................................................... 604/391
(58) Field of Search ..................... 604/385.01, 385.04, 604/386–387, 389–391

(56) References Cited

U.S. PATENT DOCUMENTS

| 4,887,602 | A | * | 12/1989 | O'Leary ................. 604/385.25 |
| 5,545,159 | A | | 8/1996 | Lancaster et al. |
| 5,846,232 | A | | 12/1998 | Serbiak et al. |
| 5,906,008 | A | * | 5/1999 | Heki et al. ...................... 2/110 |
| 5,997,981 | A | | 12/1999 | McCormack et al. |
| 6,027,484 | A | * | 2/2000 | Romare ....................... 604/386 |
| 6,258,076 | B1 | * | 7/2001 | Glaug et al. ................. 604/387 |

FOREIGN PATENT DOCUMENTS

WO    WO 01/12427    2/2001

* cited by examiner

*Primary Examiner*—Weilun Lo
*Assistant Examiner*—Catharine L. Anderson
(74) *Attorney, Agent, or Firm*—Butzel Long

(57) ABSTRACT

A disposable diaper having a pair of rear wings that partially extend outward in a circumferential direction to form fastener sections. The wings are formed on inner surfaces thereof with a plurality of fine depressions. The number of these depressions per unit area on the inner surfaces of the respective rear wings is less in regions adapted to be engaged with the male members of the respective fastener sections as these fastener sections are folded back onto the inner surfaces of the respective rear wings than in the remaining region.

5 Claims, 7 Drawing Sheets

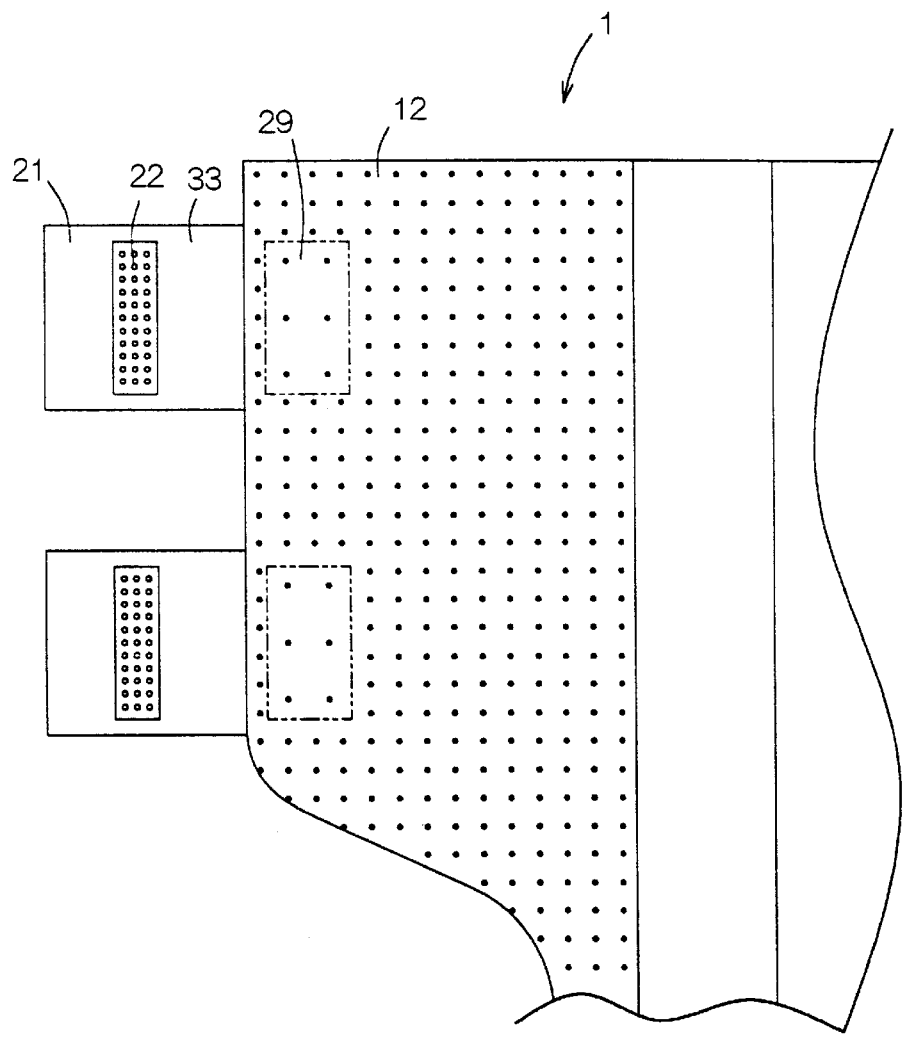

DISPOSABLE DIAPER

BACKGROUND OF THE INVENTION

This invention relates to a disposable diaper provided in a rear waist region with a pair of wings.

Conventional disposable diapers are provided in rear waist regions with a pair of wings. In such a diaper, the wings are provided on circumferential edges thereof with fasteners serving to connect the front and rear waist regions to each other. The fasteners may be usually provided in the form of an adhesive tape or male members of so-called mechanical fasteners. The inner surfaces of the wings are often formed with a nonwoven fabric in order to avoid an anxiety that the inner surfaces might irritate the skin of a diaper wearer.

If the male members of so-called mechanical fasteners are used as the fasteners in the diaper of prior art, these fasteners will be preferably held by being folded back onto the inner surfaces of the respective wings and releasably engaged with a nonwoven fabric of the wings in the course from its production until actual use of the diaper. Thereby handling of the diaper is facilitated for both the manufacturer and the consumers. During adjustment of the diaper, particularly for a bedridden adult, the wings are sometimes vigorously pulled for putting on or taking off of the diaper. Taking this into account, the nonwoven fabric forming the wings must have a sufficient strength to resist such pulling force. One of means useful to improve a strength of the nonwoven fabric is embossing of the nonwoven fabric under heating. However, use of such means disadvantageously decreases a fluffiness of the nonwoven fabric and deteriorates an effect of the engagement between the male members of the mechanical fasteners and the respective wings.

SUMMARY OF THE INVENTION

It is an object of this invention to provide a diaper having wings that are sufficiently strong to resist pulling forces and configured so that male members of mechanical fasteners may be more easily engaged with component fibers of a nonwoven fabric, which form the wings.

According to this invention, there is a disposable diaper comprising a liquid-pervious topsheet, a liquid-impervious backsheet and a liquid-absorbent core disposed between these two sheets so as to configure a front waist region, a rear waist region and a crotch region extending between these two waist regions in a longitudinal direction of the diaper wherein the rear waist region is formed on transversely opposite side portions thereof with wings extending outward in a circumferential direction intersecting the longitudinal direction and the wings are formed with fastener sections extending outward in the circumferential direction and provided on inner surfaces thereof with male members as components of so-called mechanical fasteners.

According to this invention, each of the wings has inner and outer surfaces of which at least the inner surface is defined by a nonwoven fabric and the nonwoven fabric is formed with a plurality of fine depressions in such a distribution that the number of the fine depressions per unit area of the wing is less in a region of the nonwoven fabric destined to be engaged with the male member than in the remaining region of the wing.

BRIEF DESCRIPTION OF THE DRAWINGS

FIG. 7 is a view similar to FIG. 3 but showing further another embodiment.

DETAILED DESCRIPTION OF THE PREFERRED EMBODIMENTS

Details of the disposable diaper according to this invention will be more fully understood from the description given hereunder with reference to the accompanying drawings.

Figure 1:
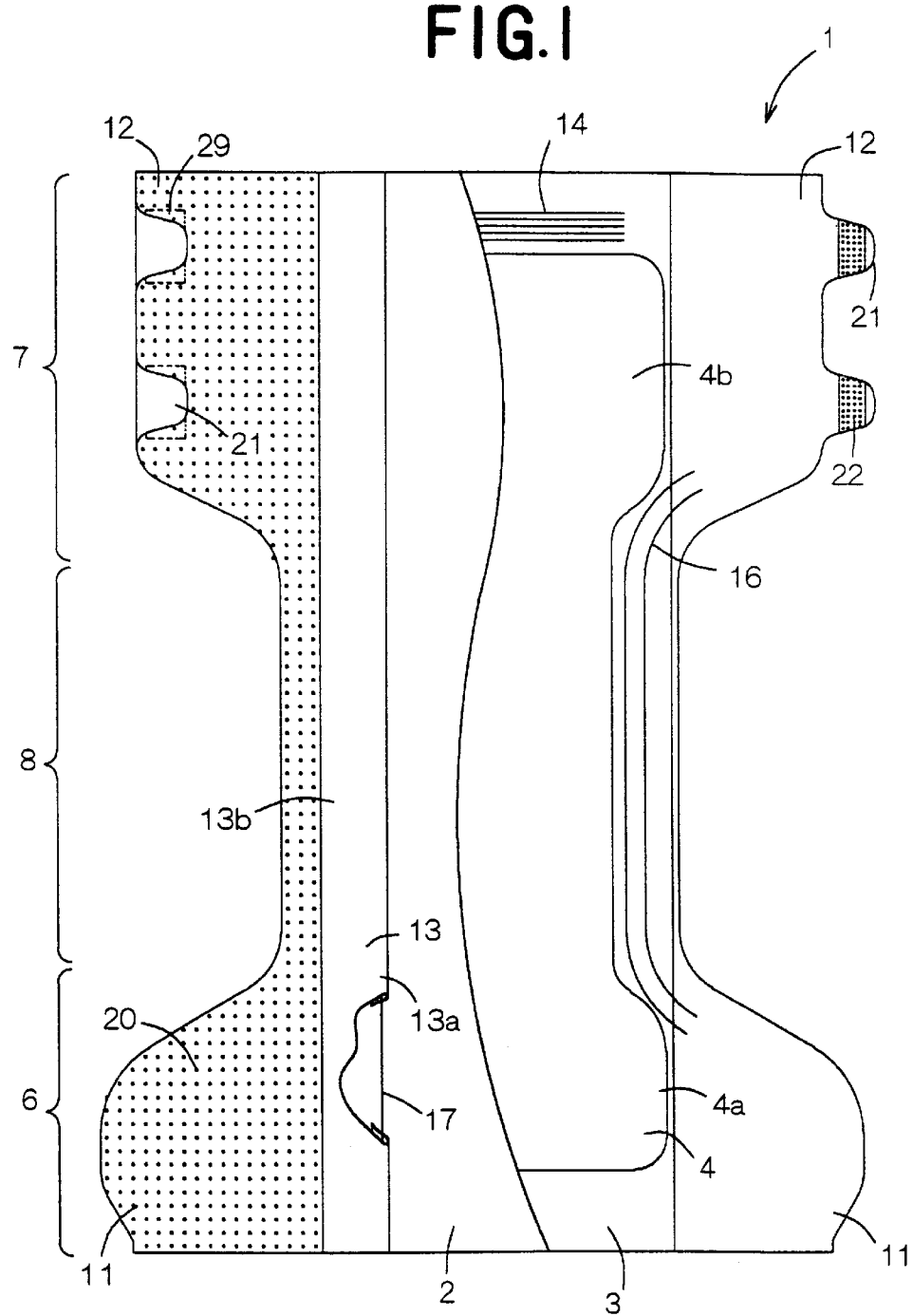
FIG. 1 is a plan view showing an inner side of the disposable diaper as partially broken away.
Figure 2:
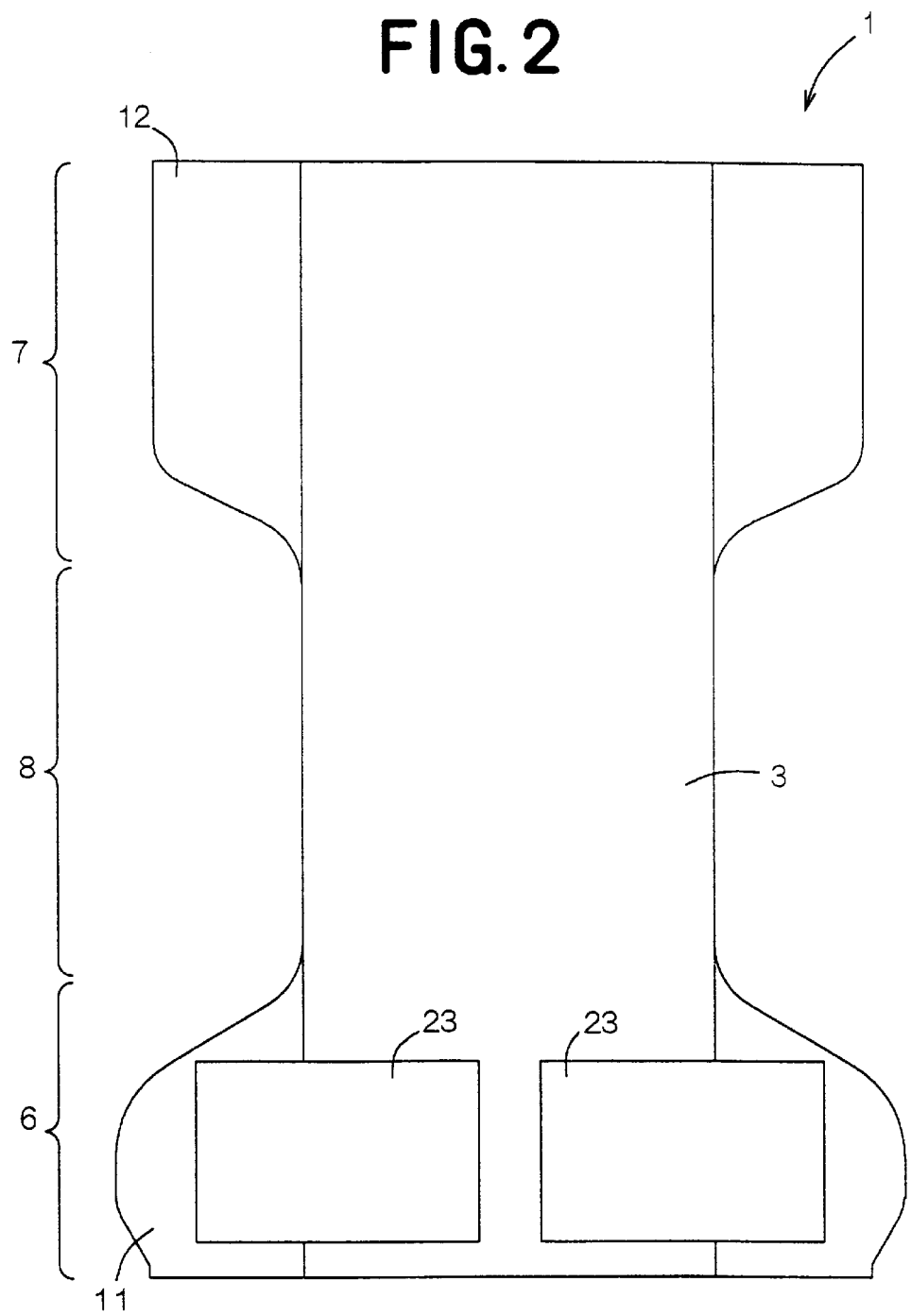
FIG. 2 is a plan view showing an outer side of the disposable diaper.

FIG. 1 is a plan view showing an inner side of a diaper 1 as partially broken away and FIG. 2 is a plan view showing an outer side of the diaper 1. The diaper 1 has a liquid-pervious topsheet 2, a liquid-impervious backsheet 3 and a liquid-absorbent core 4 disposed between these two sheets 2, 3. The diaper 1 is longitudinally (i.e., vertically as viewed in these figures) composed of a front waist region 6, a rear waist region 7 and a crotch region 8 extending between these two waist regions 6, 7. The front and rear waist regions 6, 7 are respectively formed with front wings 11 and rear wings 12 extending circumferentially outward from transversely opposite side edges thereof. The front and rear wings 11, 12 and transversely opposite side portions of the crotch region 8 are formed with a plurality of fine depressions 20. Along an outer end of the rear waist region 7, a plurality of elastic members 14 extend circumferentially of the region 7 to be associated with a waist-opening. The crotch region 8 is provided along transversely opposite side edges thereof with a plurality of elastic members 16 extending longitudinally of the region 8 to be associated with respective leg-openings. These elastic members 14, 16 are disposed between the top- and backsheets 2, 3 or between separately prepared sheets that are bonded to these top- and backsheets 2, 3, respectively, so as to extend and be bonded under tension to one of these sheets.

A pair of ribbon-like barrier cuffs 13 longitudinally extend on the inner surface of the diaper 1 in parallel to transversely opposite side edges of the diaper 1, respectively. Each of the barrier cuffs 13 has its outer side edge portion 13b as well as its longitudinally opposite end portions fixed to the inner surface of the diaper 1 and its inner side edge portion 13a not fixed to the inner surface of the diaper 1. More specifically, the inner side edge portion 13a is folded back in envelope-like manner to wrap a longitudinally extending elastic member 17 biasing the cuff 13 to rise on the inner surface of the diaper 1. The elastic member 17 is bonded under tension to the inner surface of the barrier cuff 13 at least at the longitudinally opposite end portions so that contraction of the elastic member 17 may cause the barrier cuff 13 to rise on the inner surface of the diaper 1 as the diaper 1 is put on a wearer's body. Thus, such barrier cuffs 13 are adapted to form a pair of pockets (not shown) opening inwardly of the diaper 1 and thereby to prevent body fluids from leaking.

The transversely opposite side edges of the rear wing 12 partially extend circumferentially outward to form respective pairs of fastener sections 21 spaced apart from each other vertically as viewed in FIGS. 1 and 2. Each of the fastener sections 21 is provided on its inner surface with a male member 22 as a component of a mechanical fastener so as to extend longitudinally thereof. FIG. 1 shows the left side fastener sections 21 as folded onto the inner surface of the rear wing 12 and the right side fastener sections 21 as extending circumferentially outward. As will be seen in FIG. 2, all the fastener sections 21 are folded onto the inner surfaces of the wing 12. These fastener sections 21 can be releasably anchored on the associated female members 23 at appropriate positions thereof to connect the front and rear waist regions 6, 7 to each other.

Figure 3:
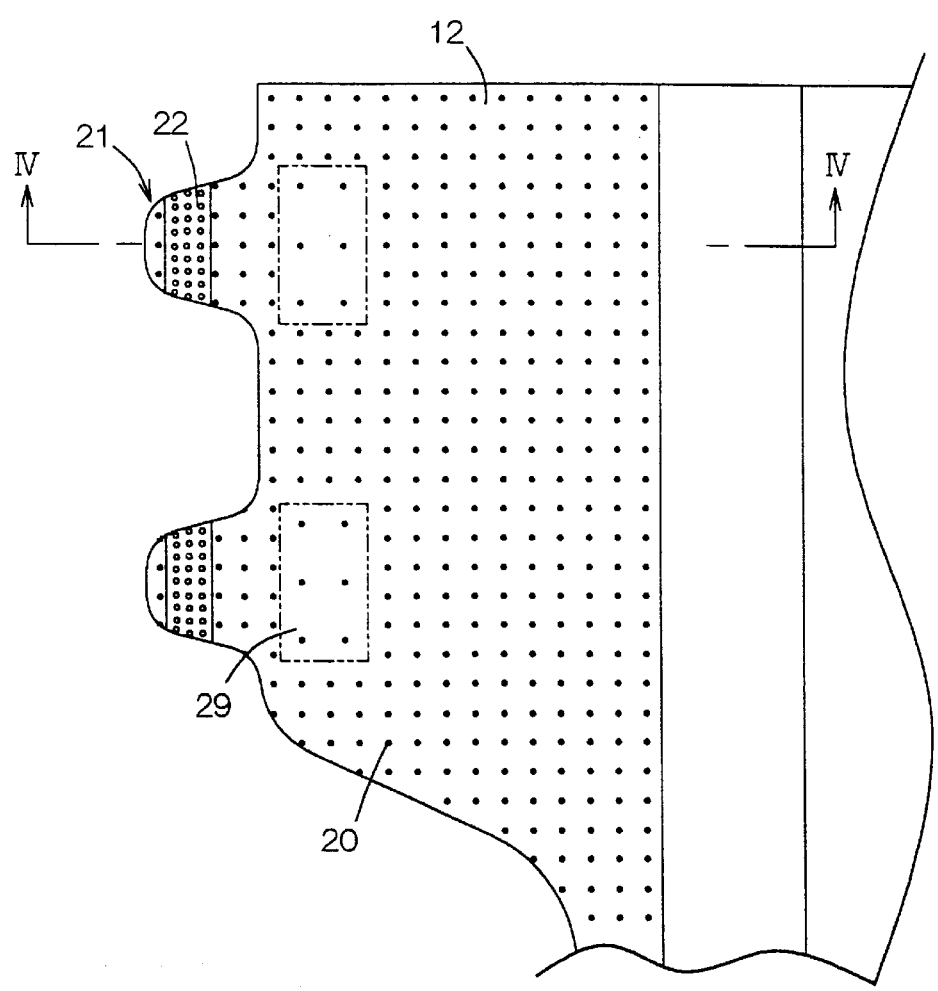
FIG. 3 is a fragmentary diagram showing a rear wing in an enlarged scale.
Figure 4:
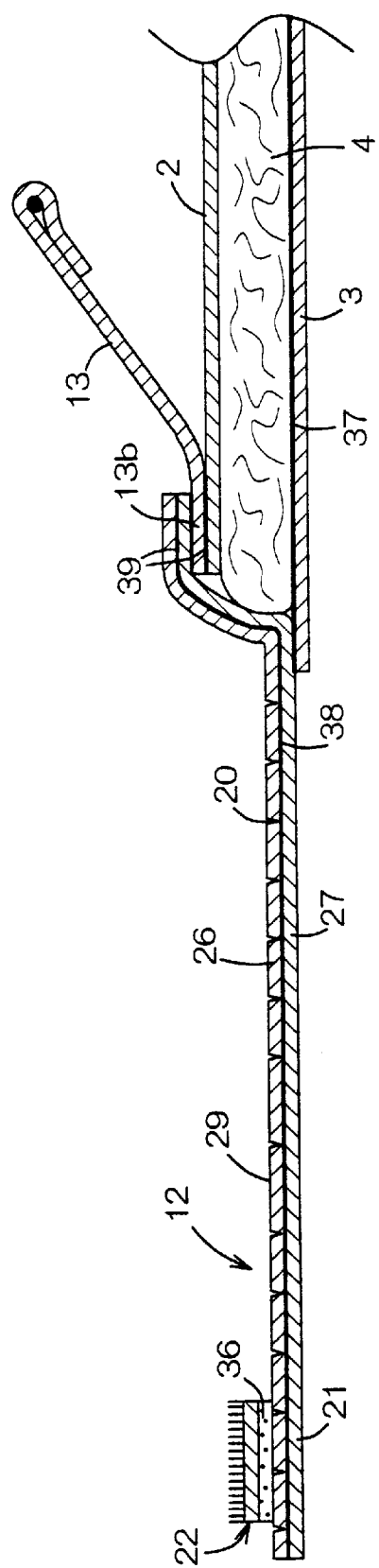
FIG. 4 is a sectional view taken along a line IV—IV in FIG. 3.

FIG. 3 is a fragmentary plan view of the diaper 1 showing the rear wing 12 in an enlarged scale and FIG. 4 is a sectional view taken along a line IV—IV in FIG. 3. Referring to FIGS. 3 and 4, the fastener sections 21 extend outward in a circumferential direction. The rear wing 12 comprises an inside a nonwoven fabric layer 26 defining the inner side of the diaper 1 and an outer side nonwoven fabric layer 27 defining the outer side of the diaper 1. These two nonwoven fabric layers 26, 27 are bonded to each other by means of hot melt adhesive 38. The fastener sections 21 extending from the rear wing 12 are formed as partial extensions of the inner and outer side nonwoven fabric layers 26, 27 and the male members 22 bonded to the inner side nonwoven fabric layer 26 by means of adhesive 36. These male members 22 are releasably engaged with respective fastener holding zones 29 as the fastener sections 21 are folded back onto the inner surface of the diaper 1 (See FIG. 1).

The rear wing 12 is formed on its substantially entire inner side nonwoven fabric layer 26 inclusive of the fastener sections 21 with a plurality of fine depressions 20. These fine depressions 20 may be formed by partially pressing the inner side nonwoven fabric layer 26 preferably at a temperature sufficiently high to soften or melt thermoplastic synthetic fibers constituting the inner side nonwoven fabric layer 26. In the depressions 20, the pressed fibers are more closely contacting together and are more tightly intertwined and/or fused together than in the remaining region. Such intertwinement and/or fusion restrain mutual movement of the component fibers of the inner side nonwoven fabric layer 26 and improve the tensile strength as well as the rigidity thereof. With an advantageous consequence, it is unnecessary for the rear wings 12 of this diaper 1 to use a large amount of a nonwoven fabric having a high basis weight in order to improve the tensile strength. However, a plurality of the depressions 20 inevitably make the component fibers of the inner side nonwoven fabric layer 26 less fluffy and thereby makes it difficult to bring the male members 22 in engagement with the inner side nonwoven fabric layer 26. This invention solves this problem by an arrangement such that the number of the depressions 20 per unit area of the rear wing 12 (i.e., density of the depressions 20) is less in the fastener holding zones 29 than in the remaining region. In the case of the inner side nonwoven fabric layer 26 made of polypropylene fiber having a basis weight of 10~100 g/m², for example, an occupancy ratio of the depressions 20 each having a diameter of 0.2~1.5 mm to the total area of the rear wings may be set to 10·50%. Such occupancy ratio in the fastener holding zones 29 may be set to a value 5·20% lower than the occupancy ratio in the region surrounding the fastener holding zones 29.

With the rear wings 12 arranged as has been described above, a relatively low tensile strength of the inner side nonwoven fabric layer 26 is increased by formation of the depressions 20. In addition, an anxiety that the anchoring effect of the male members 22 might be deteriorated due to formation of these depressions 20 is eliminated by formation of the adequately fluffy target fastener holding zones 29. Even if the fastener holding zones 29 have a relatively low tensile strength, there is no apprehension that the tensile strength of the rear wings 12 might be thereby remarkably deteriorated. This is for the reason that the region of the rear wings 12 surrounding the fastener holding zones 29 has the depressions 20 distributed at a sufficiently high density to ensure a desired hi h tensile strength.

In the case of the diaper 1 exclusively used by an adult, particularly by a bedridden adult, the rear wings 12 must be sometimes vigorously pulled for putting on or taking off of the diaper 1. However, use of a nonwoven fabric having a relatively high basis weight as stock material for the rear wings 12 taking account of this is not favorable from the viewpoint of material cost. However, the ability to improve the tensile strength by formation of the depressions 20 is significant.

In the diaper 1, the front wings 11 as well as the transversely opposite side portions of the crotch region 8 are constructed in a substantially same manner as the rear wings 12. More specifically, the inner side nonwoven fabric layer 26 and the outer side nonwoven fabric layer 27 are bonded to each other by means of adhesive 38 and the depressions 20 are distributed therein at a high density. In the crotch region 8, the inner side nonwoven fabric layer 26 stiffened due to formation of the depressions 20 may sometimes stimulate skin of the diaper wearer. If there is such apprehension, a density at which the depressions 20 are distributed in the crotch region 8 may be set to the level which is same as or lower than in the fastener holding zones 29. The inner and outer side nonwoven fabric layers 26, 27 forming these front and rear wings 11, 12 and the transversely opposite side portions of the crotch region 8 are bonded to the outer side edge portions 13b of the barrier cuffs 13 preferably formed with liquid-impervious sheets using hot melt adhesive 39 or heat-sealing technique. Adhesive 36~39 used to assemble the diaper 1 may be intermittently applied to the respective members in the longitudinal direction and/or in the circumferential direction.

Figure 5:
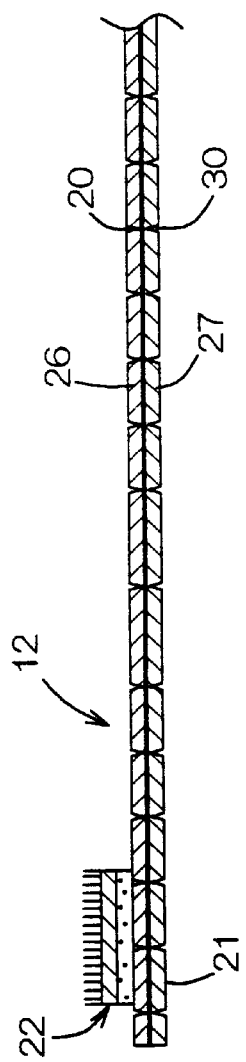
FIG. 5 is a view similar to FIG. 4 but showing another embodiment.

FIG. 5 is a view similar to FIG. 4 but showing another embodiment of this invention. In the rear wings 12 of the diaper 1, the inner side nonwoven fabric layer 26 is formed with a plurality of depressions 20 and the outer side nonwoven fabric layer 27 is formed with a plurality of depressions 30. Positional relationship beetweeen the depressions 20 and 30 is optional, i.e., the depressions 20 may be vertically aligned with the depressions 30 as seen in FIG. 5 or each of the depressions 30 may be interposed between each pair of the depressions 20, 20 which are adjacent to each other in transverse direction as viewed in FIG. 5. The depressions 30 serve to improve a tensile strength of the outer side nonwoven fabric layer 27 and at the same time to improve a stiffness of the rear wings 12. Concerning the depth of these depressions 20, 30, the arrangement shown by FIG. 5 may altered so that these depressions 20, 30 extend through the inner and outer side nonwoven fabric layers 26, 27. For example, the depressions 20 may extend from the inner side nonwoven fabric layer 26 to the outer side nonwoven fabric layer 27. In this case, these depressions 20, 30 serve to improve a bonding effect between these two nonwoven fabric layers 26, 27. If the bonding effect is adequately high, it is possible to eliminate interposition of adhesive 38 between these two nonwoven fabric layers 26, 27.

Figure 6:
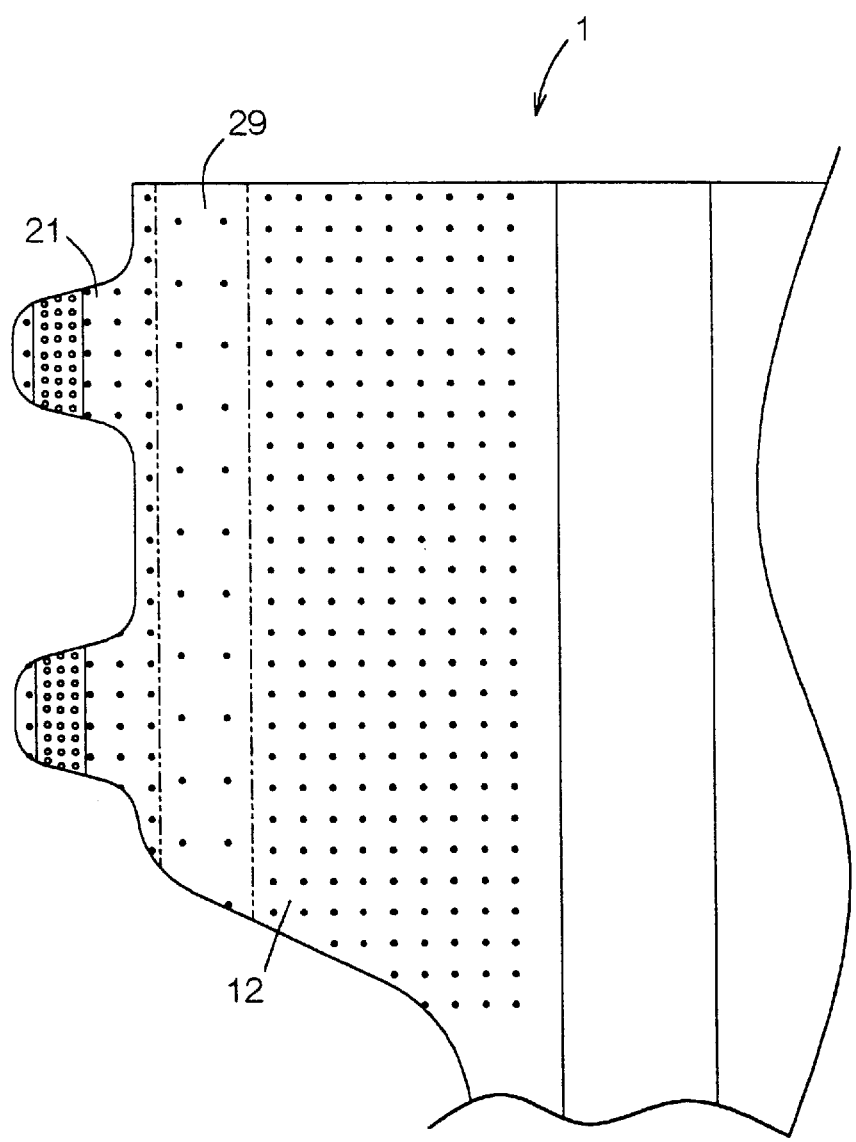
FIG. 6 is a view similar to FIG. 3 but showing still another embodiment.

FIG. 6 is a view similar to FIG. 3 but showing still another embodiment of this invention. According to this embodiment, the fastener holding zone 29 longitudinally extends on the rear wing 12 of the diaper 1. Such diaper 1 advantageously facilitates a series of steps for making the diaper 1 to be controlled since a relatively complicated operation to align the fastener sections 21 with the fastener holding zones 29 may be eliminated.

FIG. 7 is a view similar to FIG. 3 but showing further another embodiment of this invention. According to this embodiment, the rear wing 12 of the diaper 1 is provided with the fastener sections 21 formed by tape members 33 prepared separately of the wing 12 itself. The tape member 33 may be made, for example, of plastic film of which one end is fixed to the outer surface of the rear wing 12. The male member 22 as one component of so-called mechanical fastener attached to the inner surface of the tape member 33 is adapted to be anchored on the zone 29 of the rear wing 12.

In the embodiments of this invention as have been described above, it is possible to form the rear wings 12, the front wings 11 and the side portions of the crotch region 8, which are formed with the inner and outer side nonwoven fabric layers 26, 27, by the inner side nonwoven fabric layer 26 alone. It is also possible to replace the rear wings 12 by the front wings 11 and to replace the front wings 11 by the rear wings for implementation of this invention.

In the disposable diaper according to this invention, the rear wings formed with a nonwoven fabric is formed on its inner surface with a plurality of fine depressions distributed at a sufficiently high density to improve a strength of the wings, on one hand, and the fine depressions are distributed at a relatively low density in the fastener holding zones destined to be engaged with the male members of the mechanical fasteners, on the other hand. This unique arrangement improves a tensile strength of the rear wings and facilitate the fastener sections to be anchored on the fastener holding zones.

What is claimed is:

1. An open-type disposable diaper comprising:

a liquid-pervious topsheet;

a liquid-impervious backsheet;

a liquid-absorbent core disposed between said liquid-pervious backsheet and said liquid-impervious backsheet;

a front waist region;

a rear waist region;

a crotch region extending between said front waist region and said rear waist region in a longitudinal direction of the diaper;

wings formed on transversely opposite side portions of said rear waist region and extending outward in a circumferential direction intersecting said longitudinal direction; and fastener sections formed on said wings and extending outward in said circumferential direction and provided on inner surfaces thereof with male mechanical members, said fastener sections configured to connect side portions of the front and rear waist regions of said diaper together, each of said wings having inner and outer surfaces of which at least said inner surfaces comprises a nonwoven fabric, said nonwoven fabric being formed with a plurality of spaced apart fine depressions that comprise an may that extends coextensively with the entire inner surface of each of the wings, said plurality of fine depressions being arranged so that there are less of said plurality of fine depressions per unit area in a region of said wings which is configured to be engaged by said male mechanical fastener members than in another region of said wings.

2. The diaper according to claim 1, wherein said region of said wings which is configured to be engaged by said male mechanical fasteners members is surrounded by said another region of said wings.

3. The diaper according to claim 1, wherein said nonwoven fabric comprises component fibers that are fused together in said plurality of fine depressions.

4. The diaper according to claim 1, wherein said nonwoven fabric comprises component fibers that are more densely gathered in each of said plurality of fine depressions than in regions surrounding each of said plurality of fine depressions.

5. The diaper according to claim 1, wherein each of said wings comprises an inner side nonwoven fabric that defines an inner surface of said wing and an outer side nonwoven fabric that defines an outer surface of said wing, said inner and outer side nonwoven fabrics being bonded together at said plurality of fine depressions.

* * * * *